(12) United States Patent
Bartel et al.

(10) Patent No.: US 7,166,106 B2
(45) Date of Patent: Jan. 23, 2007

(54) BIPOLAR CLAMP

(75) Inventors: Volker Bartel, Bodelshausen (DE); Jürgen Hiller, Dettingen/Erms (DE)

(73) Assignee: Erbe Elektromedizin GmbH, Tubingen (DE)

( * ) Notice: Subject to any disclaimer, the term of this patent is extended or adjusted under 35 U.S.C. 154(b) by 467 days.

(21) Appl. No.: 10/480,010

(22) PCT Filed: Jun. 4, 2002

(86) PCT No.: PCT/EP02/06141

§ 371 (c)(1),
(2), (4) Date: Dec. 4, 2003

(87) PCT Pub. No.: WO02/098313

PCT Pub. Date: Dec. 12, 2002

(65) Prior Publication Data

US 2004/0153020 A1 Aug. 5, 2004

(30) Foreign Application Priority Data

Jun. 5, 2001 (DE) ............................. 101 27 259
Feb. 7, 2002 (DE) ............................. 102 05 093

(51) Int. Cl.
*A61B 18/18* (2006.01)
(52) U.S. Cl. ............................. 606/51; 606/45; 606/49; 606/50; 606/52
(58) Field of Classification Search ............ 606/50–52
See application file for complete search history.

(56) References Cited

U.S. PATENT DOCUMENTS 3,100,489 A * 8/1963 Bagley .................. 606/42

(Continued)

FOREIGN PATENT DOCUMENTS

DE 92 04 553 U1 6/1992

(Continued)

OTHER PUBLICATIONS

International Search Report in PCT/EP02/06141 dated Oct. 7, 2002.

(Continued)

*Primary Examiner*—Michael Peffley
*Assistant Examiner*—Alex Toy
(74) *Attorney, Agent, or Firm*—Marshall, Gerstein & Borun LLP

(57) ABSTRACT

The invention relates to a bipolar clamp (10) comprising two scissor members (12, 14), which are joined together mechanically by means of an insulating screw or similar pivot joint (16) about which they can rotate with respect to one another, but are electrically insulated from one another,
  electrode components (18, 20) at distal ends (22, 24) of the scissor members (12, 14) for grasping tissue and conducting an electrical current through the tissue to cause. coagulation,
  handle devices (26, 28) at proximal ends (30, 32) of the scissor members (12, 14),
  current-supply means (34, 40, 42) at the proximal end (32) of one scissor member (14)
  ratchets (36, 38) between the pivot joint (16) and the proximal ends (32, 34) to lock, the scissor members (12, 14) to one another in a closed position.

In accordance with the invention the current-supply means (34, 40, 42) are so disposed, and the ratchets (36, 38) are so constructed, that current flow from the current-supply means (34, 40, 42) to the electrode components (18, 20) is possible only in the closed position. These measures make manipulation of the bipolar clamp (10) safer, because a coagulation current cannot flow until the clamp is in the closed position.

10 Claims, 3 Drawing Sheets

U.S. PATENT DOCUMENTS

| | | | | |
|---|---|---|---|---|
| 4,274,413 A | * | 6/1981 | Hahn et al. | 606/42 |
| 4,370,980 A | | 2/1983 | Lottick | 128/303.17 |
| 5,026,370 A | | 6/1991 | Lottick | 606/42 |
| 5,122,139 A | * | 6/1992 | Sutter | 606/51 |
| 5,342,391 A | * | 8/1994 | Foshee et al. | 606/205 |
| 6,050,996 A | * | 4/2000 | Schmaltz et al. | 606/51 |
| 6,053,914 A | * | 4/2000 | Eggers et al. | 606/48 |
| 6,334,861 B1 | * | 1/2002 | Chandler et al. | 606/50 |
| 6,352,536 B1 | * | 3/2002 | Buysse et al. | 606/51 |

FOREIGN PATENT DOCUMENTS

| | | |
|---|---|---|
| DE | 197 51 108 A1 | 5/1999 |
| EP | 0 717 960 A2 | 6/1996 |
| JP | HEI06-500476 | 1/1994 |
| WO | WO-91/16859 | 11/1991 |
| WO | WO 99/23933 A2 | 5/1999 |
| WO | WO 99/23933 A3 | 5/1999 |
| WO | WO 99/23959 | 5/1999 |

OTHER PUBLICATIONS

International Preliminary Examination Report in PCT/EP02/06141 dated Jul. 14, 2003.

English translation of International Preliminary Examination Report issued in PCT/EP02/06141.

English translation of Japanese office action, Japanese Patent Application No. 2003-501359, dispatched Jun. 23, 2006.

* cited by examiner

BIPOLAR CLAMP

RELATED U.S. APPLICATIONS

This is the U.S. national phase of International Application No. PCT/EP02/06141 filed Jun. 4, 2002 and designating the U.S., the entire disclosure of which is incorporated herein by reference.

FIELD OF THE INVENTION

The invention relates to a bipolar clamp comprising two clamp members which are pivotally joined together and which, at the distal ends of the clamp members, are provided with electrode components for grasping tissue and conducting an electrical current through the tissue to cause coagulation.

BACKGROUND OF THE INVENTION

Such bipolar clamps are known, for example, from the PCT applications WO99/23933 and WO99/23959. They consist substantially of two clamp members joined together mechanically by means of an insulating screw or similar pivot joint, about which they can rotate with respect to one another, but are electrically insulated from one another. At the distal ends of the clamp members are provided electrode components for grasping tissue and conducting an electrical current through the tissue to cause coagulation. For manipulation of the bipolar clamp, the clamp members comprise handle devices at their proximal ends. The coagulation current is supplied by way of current-supply terminals at the proximal end of at least one clamp member. So that the bipolar clamp can be locked in a closed position, interlocking ratchets are disposed between the pivot joint and the proximal ends of the clamp members. This measure ensures that when the clamp is in the closed position, it holds the tissue securely.

However, the bipolar clamp disclosed in WO99/23933 presents two disadvantages.

First, the current supply is provided at only one clamp member; more precisely, from a terminal attached to the handle device disposed at the proximal end of the clamp member the current is supplied by two wires that follow a common route approximately as far as the pivot joint between the two clamp members. From that point on, the wires run separately to the electrodes to which they are electrically connected. Although this makes manipulation of the clamp easier, the arrangement of the wires in particular near the joint connecting the clamp members makes them vulnerable to wear and tear, especially when the clamp is frequently used; a fracture can appear in the electrical leads. Because of the severe mechanical loading of this kind of clamp, such an event is highly likely.

Furthermore, it is possible for a coagulation current to flow even before the clamp members have been locked in the closed position, because the time when current flows is determined by the operator. Therefore the operator must essentially perform three manipulations to coagulate tissue: grasping the tissue, locking the clamp members together and activating the current flow. This complicates the operation. The main problem is that the operator can easily activate the current by accident before the locking is completed, inducing an unintended coagulation.

BRIEF SUMMARY OF THE INVENTION

It is thus the object of the present invention to develop the known bipolar clamp further, primarily so that it can be manipulated more reliably as well as more simply.

According to the present invention there is provided a bipolar clamp comprising
- two clamp members, which are joined together mechanically by means of an insulating pivot joint about which they can rotate with respect to one another, but are electrically insulated from one another,
- electrode components at distal ends of the clamp members for grasping tissue and conducting an electrical current through the tissue to cause coagulation,
- handle devices at proximal ends of the clamp members,
- current-supply means for supplying the electrical current to the electrode components, and
- ratchets which are located between the pivot joint and the proximal ends of the clamp members to lock the clamp members to one another when in a closed position, and which are constructed such that current flow from the current-supply means to the electrode components is possible only when the ratchets are in their closed position.

The invention is based on the idea of arranging the current-supply devices, and constructing the ratchets, in such a way that current flow through the current-supply devices to the electrode parts is possible only in the closed position. By this means an especially safe bipolar clamp is created, because current cannot flow until tissue has been grasped with the clamp and the clamp has been locked into the closed position. In other words, coagulation of tissue can occur only after the tissue is securely held by the clamp, between its two jaws. Thus a too-early passage of coagulation current into tissue that is to be grasped is reliably prevented. Furthermore, the manipulation is simplified because in principle the current flow is controlled by the locking of the clamp members. That is, an operator needs only to grasp the tissue that is to be coagulated and lock the clamp members together, in order to bring about coagulation.

According to the invention the bipolar clamp comprises two clamp members, which are mechanically joined to one another by means of an insulating screw or similar pivot joint so that they can be rotated with respect to one another, but are electrically insulated from one another. At distal ends of the clamp members are provided electrode components for grasping tissue and conducting an electrical current through the tissue to cause coagulation. The proximal ends of the clamp members comprise handle devices that allow the bipolar clamp to be manipulated in a simple manner. In addition, current-supply means are provided, through which the coagulation current can be conducted. Between the pivot joint and the proximal ends interlocking ratchets are provided, for the purpose of locking the clamp members to one another in a closed position. The current-supply means are so arranged, and the ratchets so constructed, that a flow of current from the current-supply terminals to the electrode elements is possible only in the closed position.

Preferably the current-supply terminals are disposed at the proximal end of a clamp member; the ratchets then form a conducting section of the current-supply means. As a result, the current-supply devices can be separated from one another in the proximal region of one of the clamp members, far ahead of the pivot joint, so that they are substantially unaffected by actuation of the clamp. In this regard, the smooth, metallic ratchets are especially suitable to serve as a guide section for one of the current-supply devices. Above all, this arrangement avoids a bifurcation point—such as is found in the bipolar clamp disclosed in WO99/23933—where the wires serving as current-supply means, which have been running together up to the pivot joint, are diverted so as to run separately from there on. A mechanical stress is no longer imposed on the wires in the region of the joint when the clamp is opened and closed; the clamp is less subject to wear and tear, and at less risk of malfunction.

The current-supply devices can be electrical leads guided at least in certain sections outside or within the clamp members. If they run outside the clamp members, the leads should be electrically insulated as far as possible and should be fixed to the clamp member(s). The means of fixation preferably to be considered are adhesive, a clamp connection or fixation by means of special guide devices provided on one clamp member. When an electrical lead runs within a clamp member, that member must either be hollow or comprise a guide channel, for instance in the form of a bore or a groove to contain a lead.

If guide devices are used to direct the electrical leads, the clamp members preferably comprise at least in part of an electrically insulating material. In this case even bare wires can be used as current-supply devices. Then the ratchets should comprise an electrically conductive locking part and a carrier part. The locking part is attached to the carrier part in such a way that between the two parts there is a gap that can accommodate a section of an electrical lead that is electrically connected to the locking part, in particular soldered thereto.

Preferably two electrical leads are guided along the clamp member to which the current-supply terminal is attached. One of the leads is guided to the electrode component at the distal end of the clamp member carrying the current-supply terminal. The other lead is guided to the locking part of the ratchet and electrically connected thereto. The other clamp member preferably consists entirely of electrically conductive material integral with the electrode component disposed at its distal end. An electrical current thus flows by way of the ratchets or, more precisely, by way of an electrical lead as far as the locking part of the first ratchet, then through the locking part of the second ratchet and finally through the clamp member to the electrode. A bipolar clamp of this kind/can function with a minimum of electrical leads, and as a result is relatively simple in structure.

In another preferred embodiment of the clamp in accordance with the invention, the current-supply terminal is disposed at one of the ratchets; the clamp members are made of a conductive material, in particular of metal, and externally are electrically insulated; and the ratchets form a conducting section of the current-supply means. This construction produces an instrument which, in particular when metal is used for the clamp members, can bear high mechanical loads and exhibits the main advantage of the invention, namely safe manipulability. For example, a two-pole electrical plug serving as current-supply terminal can be disposed directly at one of the ratchets. Because the clamp members are made of a conductive material, they can serve to conduct the coagulation current to the electrodes. The external electrical insulation of the clamp members prevents damage to tissue that comes into contact with the clamp members. So that the coagulating function will not be possible until the clamp is in the closed position, the ratchets form a conducting section of the current-supply means. This embodiment comprises only a few parts and hence is economical on one hand, and on the other hand is little affected by wear and tear.

So that the clamp members are reliably electrically insulated from one another, the pivot joint employs as axis a peg that in one of the clamp members is seated in an insulating socket, in particular one made of ceramic. Seating in a ceramic socket offers the advantage that the pivot joint is particularly free of abrasion. Furthermore, ceramic has especially good electrically insulating properties. However, it is also possible for the insulating socket to be made of, for example, plastic, to enable economical construction of the bipolar clamp. In this case the socket should provide sufficient insulation to prevent appreciable current flow between the two clamp members through the pivot joint. In its simplest form the socket can comprise an insulating coating that presents an extremely high transition resistance to a current.

In the following an exemplary embodiment of the bipolar clamp in accordance with the invention is explained with reference to drawings, wherein

DETAILED DESCRIPTION OF THE INVENTION

Figure 1:
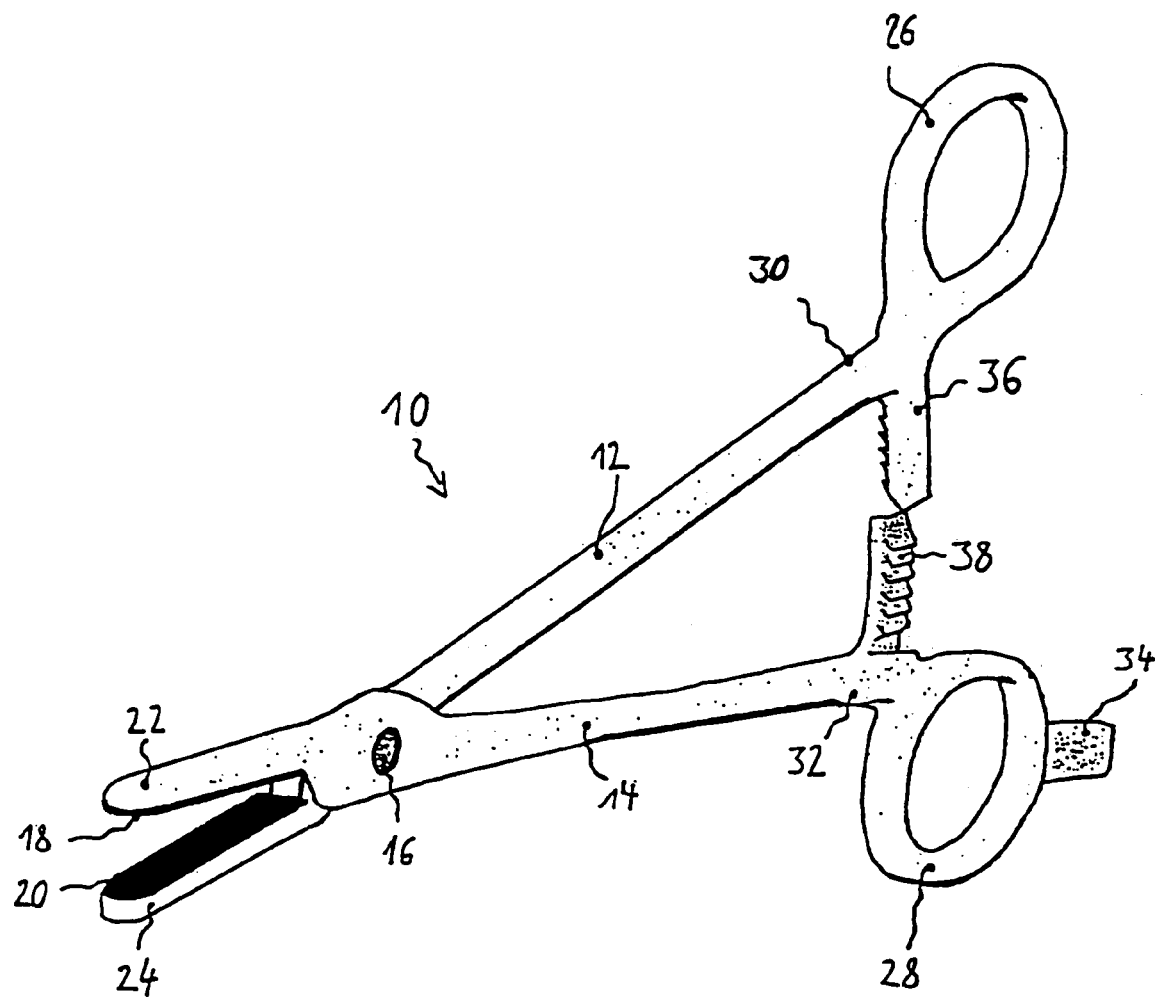
FIG. 1 shows an exemplary embodiment of the bipolar clamp in accordance with the invention.

The bipolar clamp 10 shown in perspective in FIG. 1 comprises two clamp members 12 and 14. Each of the clamp members 12 and 14 is provided at its proximal end 30 or 32, respectively, with a handle device 26 or 28. The handle devices 26 and 28 are ring-shaped like the handles of scissors, so that they can easily be manipulated by an operator. The clamp members 12 and 14 are mechanically connected by a pivot joint 16 so that they can rotate with respect to one another. The pivot joint 16 is disposed near the distal ends 22 and 24 of the clamp members 12 and 14. At the distal ends 22 and 24 of the clamp members 12 and 14 electrically conductive electrode components 20 and 18, respectively, are attached. These are used both to grasp tissue and to pass a coagulation current through the tissue. For the latter purpose, they are preferably made of metal. At the handle device 28 of the clamp member 14 terminals of the current-supply means 34 are provided. To these are connected a HF generator (not shown), which generates a high-frequency electrical coagulation current that is conducted to the electrode components 18 and 20 by way of the current-supply devices.

Figure 2:
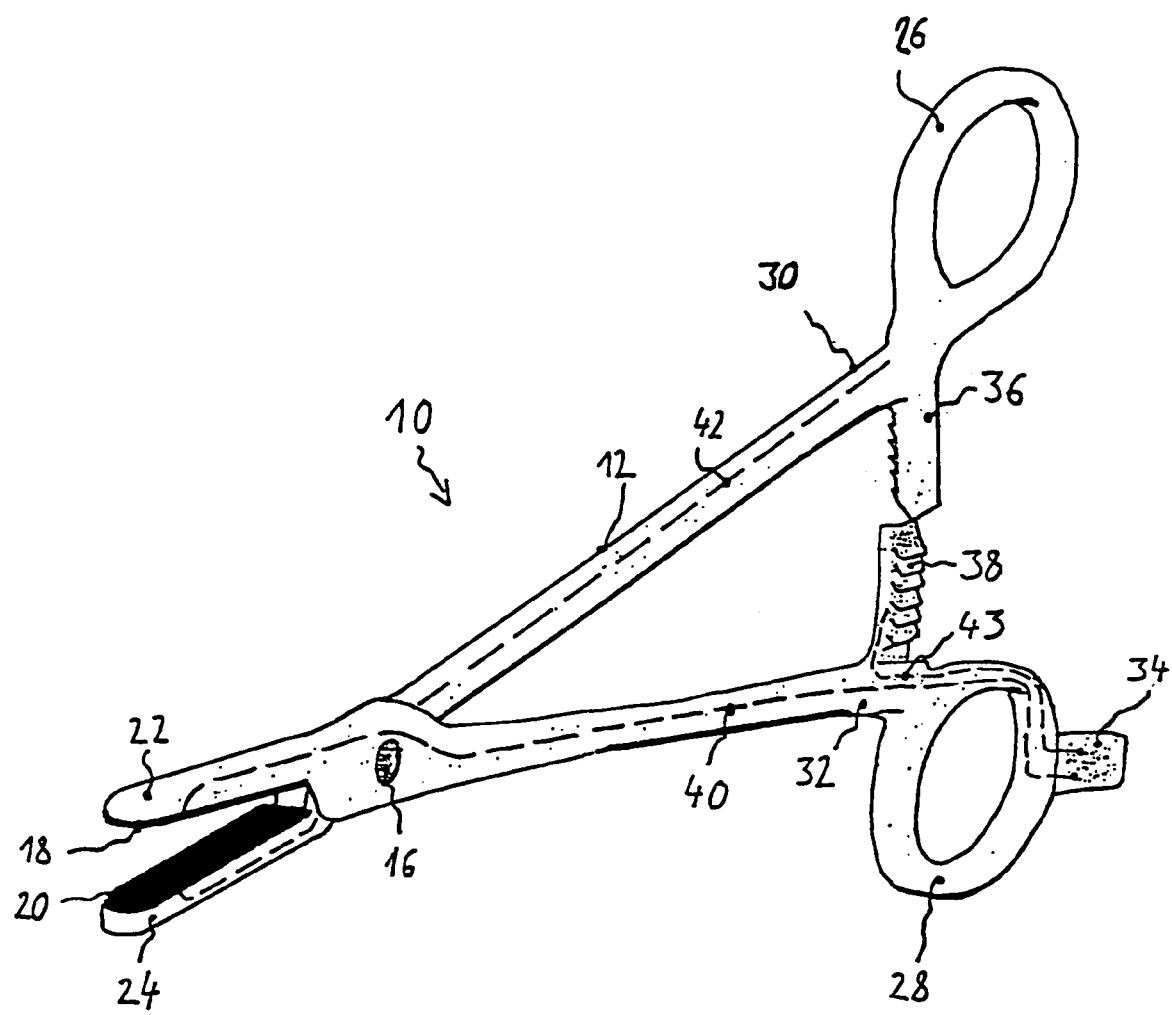
FIG. 2 shows the bipolar clamp of FIG. 1 with the electrical leads indicated by dashed lines.

FIG. 2 includes dashed lines that indicate the path along which the current-supply devices are guided in the clamp 10 shown in FIG. 1. The current-supply devices consist of electrically insulated leads 40, 42 and 43, guided in the interior of the clamp members 12 and 14. The electrical lead 43 runs from the terminal of the current-supply means 34, which is situated at the handle device 28 of the clamp member 14, to the first ratchet 38 at the proximal end 32 of the clamp member 14. Another electrical lead 42 is electrically connected at one end to the second ratchet 36 at the proximal end 30 and at its other end to the electrode component 20 at the distal end of the clamp member 12. The electrical lead 42 can be guided either along the exterior of the clamp member 12 or within the clamp member 12. The important thing here is that the electrical lead 42 is not influenced by the pivot joint 16, i.e. it is not bent during movement of the two clamp members 12 and 14. As a result, for example, the danger that the lead will break owing to frequent use of the clamp is less than is the case for the bipolar clamp known from WO99/23933. A third lead 40 runs from the terminal of the current-supply means 34 directly to the electrode component 18 at the distal end 22 of the clamp member 14. This lead 40 is also not bent when the bipolar clamp 10 is in use. In FIG. 2 the lead 40 passes over the pivot joint 16, but it can of course also be guided differently, for instance below the pivot joint 16.

Figure 3:
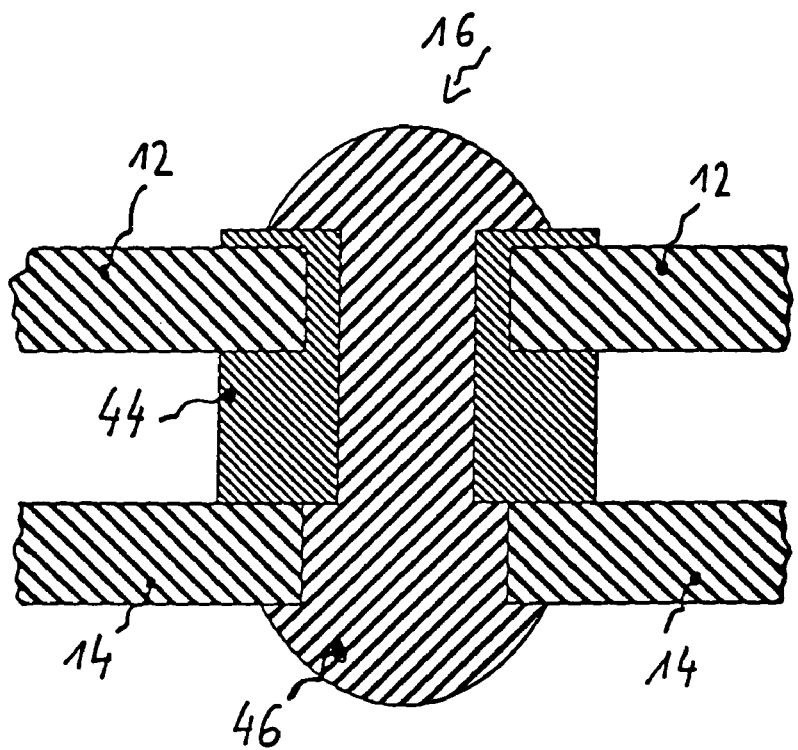
FIG. 3 is a side view of a section through the insulating pivot joint of the bipolar clamp shown in FIG. 1.

FIG. 3 shows the structure of the pivot joint 16 in detail. It comprises a pivot pin 46 which acts like a rivet to join the clamp members 12 and 14 rotatably together. One end of the pin is seated in a socket 44 that is press-fitted into an opening provided for that purpose in the clamp member 12. The socket 44 is made of an electrically insulating material, in particular ceramic. It can also consist of a material that conducts electricity only very slightly, i.e. a material with a very high electrical resistance, so that any current flowing through the pivot joint 16 from clamp member 14 to clamp member 12 or the reverse is negligibly small in comparison to the flow of coagulation current.

Figure 4:
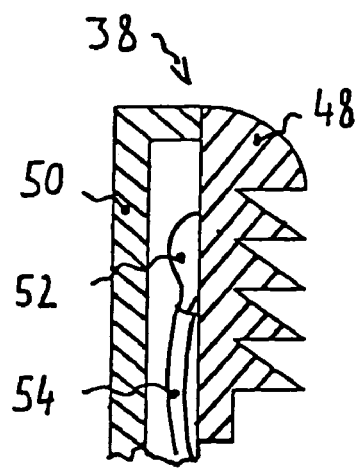
FIG. 4 shows one of the ratchets of the bipolar clamp of FIG. 2 in longitudinal section.

Finally, FIG. 4 shows in section the construction of the ratchet 38. The ratchet 38 comprises a locking part 48 mounted on a carrier part 50, which in turn is integral with the clamp member 14. The carrier part 50 consists of an insulating material. The locking part 48, which consists of a conductive material, is electrically connected by means of a solder connection 52 to a lead section 54 of the electrical lead 43. It can be fixed to the carrier part 50 in particular by adhesive or by clamping.

LIST OF REFERENCE NUMERALS

10 Bipolar clamp
12 Clamp member
14 Clamp member
16 Insulating pivot joint
18 Electrode component
20 Electrode component
22 Distal end of a clamp member
24 Distal end of a clamp member
26 Handle device
28 Handle device
30 Proximal end of a clamp member
32 Proximal end of a clamp member
34 Terminal of current-supply means
36 Ratchet
38 Ratchet
40 Electrical lead
42 Electrical lead
43 Electrical lead
44 Insulating socket
46 Pin
48 Locking part
50 Carrier part
52 Solder connection
54 Lead section

The invention claimed is:

1. Bipolar clamp comprising:
   two clamp members, that are joined together mechanically by means of an insulating pivot joint about which they can rotate with respect to one another, but that are electrically insulated from one another,
   electrode components at distal ends of the clamp members for grasping tissue and conducting an electrical current through the tissue to cause coagulation,
   handle devices at proximal ends of the clamp members,
   current-supply means for supplying the electrical current to the electrode components, wherein the current-supply means is disposed at the proximal end of one of the clamp members, and
   ratchets which are located between the pivot joint and the proximal ends of the clamp members to lock the clamp members to one another when in a closed position, wherein the ratchets form a conducting section of the current-supply means and are constructed such that current flow from the current-supply means to the electrode components is possible only when the ratchets are in their closed position.

2. Bipolar clamp according to claim 1, wherein the current-supply means includes electrical leads that at least in sections are guided along the clamp members.

3. Bipolar clamp according to claim 2, wherein the clamp members are comprised at least in part of an electrically insulating material and the electrical leads are guided by guide devices defined by the clamp members in the form of at least one of a groove, a bore and a channel.

4. Bipolar clamp according to claim 3, wherein at least one of the ratchets comprises an electrically conductive locking part and a carrier part, the locking part being fixed to the carrier part in such a way that between the locking and carrier parts is defined a gap to accommodate a section of an electrical lead that is electrically connected to the locking part.

5. Bipolar clamp according to claim 4, wherein two electrical leads are guided within the one of the clamp members containing the current-supply means, of which one runs to and is electrically connected to the electrode component at the distal end of the clamp member and the other runs to and is electrically connected to the locking part of the ratchet, the other clamp member being made of an electrically conductive material.

6. Bipolar clamp according to claim 1, wherein the current-supply means is disposed at one of the proximal ends of the clamp members, the clamp members are made of an electrically conductive material and externally are electrically insulated, and the ratchets form a conducting section of the current-supply means.

7. Bipolar clamp according to claim 1, wherein the electrically insulating pivot joint comprises a pin which acts as an axis of rotation and which is seated in one of the clamp members within an electrically insulating socket.

8. Bipolar clamp, comprising:
   two clamp members, that are joined together mechanically by means of an insulating pivot joint about which they can rotate with respect to one another, but that are electrically insulated from one another,
   electrode components at distal ends of the clamp members for grasping tissue and conducting an electrical current through the tissue to cause coagulation,
   handle devices at proximal ends of the clamp members,
   current-supply means for supplying the electrical current to the electrode components, wherein the current-supply means includes two or more electrical leads that at least in sections are guided along the clamp members, and
   two or more ratchets which are located between the pivot joint and the proximal ends of the clamp members to lock the clamp members to one another when in a closed position, and which are constructed such that current flow from the current-supply means to the electrode components is possible only when the ratchets are in the closed position, wherein the clamp members include at least in part an electrically insulating material and the electrical leads are guided by guide devices defined by the clamp members in the form of at least one of a groove, a bore and a channel and, wherein at least one of the ratchets comprises an electrically conductive locking part and a carrier part, the locking part being fixed to the carrier part in such a way that between the locking part and the carrier part is defined a gap to accommodate a section of an electrical lead that is electrically connected to the locking part.

9. Bipolar clamp according to claim 8, wherein two of the electrical leads are guided within one of the claim members containing the current-supply means, of which one electrical lead runs to and is electrically connected to the electrode component at the distal end of the clamp member and the other electrical lead runs to and is electrically connected to the locking part of the ratchet, and wherein the other clamp member is made of an electrically conductive material.

10. Bipolar clamp, comprising:

two clamp members, that are joined together mechanically by means of an insulating pivot joint about which they can rotate with respect to one another, but that are electrically insulated from one another, electrode components at distal ends of the clamp members for grasping tissue and conducting an electrical current through the tissue to cause coagulation, handle devices at proximal ends of the clamp members, current-supply means for supplying the electrical current to the electrode components, and ratchets which are located between the pivot joint and the proximal ends of the clamp members to lock the clamp members to one another when in a closed position, and are constructed such that current flow from the current-supply means to the electrode components is possible only when the ratchets are in their closed position, wherein the current-supply means is disposed at one of the proximal ends of the clamp members, the clamp members are made of an electrically conductive material and externally are electrically insulated, and the ratchets form a conducting section of the current-supply means.

* * * * *